United States Patent
Kim

(10) Patent No.: US 11,109,845 B2
(45) Date of Patent: Sep. 7, 2021

(54) URINE TEST CONTAINER FOR URINE SEPARATION AND INFECTION CONTROL

(71) Applicant: THE CATHOLIC UNIVERSITY OF KOREA INDUSTRY-ACADEMIC COOPERATION FOUNDATION, Seoul (KR)

(72) Inventor: Chang Uk Kim, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 390 days.

(21) Appl. No.: 15/774,002

(22) PCT Filed: Nov. 7, 2016

(86) PCT No.: PCT/KR2016/012722
§ 371 (c)(1),
(2) Date: May 5, 2018

(87) PCT Pub. No.: WO2017/078493
PCT Pub. Date: May 11, 2017

(65) Prior Publication Data
US 2018/0317891 A1 Nov. 8, 2018

(30) Foreign Application Priority Data

Nov. 6, 2015 (KR) .......................... 10-2015-0155798
Nov. 6, 2015 (KR) .......................... 10-2015-0155800
(Continued)

(51) Int. Cl.
*A61M 5/32* (2006.01)
*A61B 10/00* (2006.01)
(Continued)

(52) U.S. Cl.
CPC .............. *A61B 10/007* (2013.01); *B01L 3/50* (2013.01); *B01L 3/502* (2013.01);
(Continued)

(58) Field of Classification Search
CPC ........... A61M 5/32; A61M 27/00; A61F 5/44; B65D 83/10; B65D 81/02
See application file for complete search history.

(56) References Cited

U.S. PATENT DOCUMENTS 3,415,299 A * 12/1968 Hinman, Jr. .............. A61F 5/44
206/324
3,874,029 A * 4/1975 McCullough ....... E05D 11/1007
16/329
(Continued)

FOREIGN PATENT DOCUMENTS

EP 0009980 A1 * 10/1979
JP 2005-517939 A 6/2005
(Continued)

*Primary Examiner* — Tatyana Zalukaeva
*Assistant Examiner* — Ilya Y Treyger
(74) *Attorney, Agent, or Firm* — Huffman Law Group, PC

(57) ABSTRACT

The present invention relates to a urine test container, Specifically, the present invention relates to a container capable of readily separating first urine while receiving whole urine in order to remove the inconvenience of discarding the first urine and putting the remaining urine in a container in a medical institution such as a hospital and a health care institution, because the quality of a test is decreased due to a plurality of epithelial cells included in the first urine in a urine test. A container for collecting the urine of a subject, which is one aspect of the present invention, comprises: a container for collecting urine; and a barrier film located within the container so as to divide the inside of the container, thereby separating a predetermined amount of the first urine, which is first collected from the urine, and the second urine differing from the first urine, wherein only the
(Continued)

second urine is used in the urine test of the subject and the first urine and the second urine can be separated using the barrier film.

19 Claims, 13 Drawing Sheets

(30) Foreign Application Priority Data

Jan. 15, 2016 (KR) .................. 10-2016-0005242
Jan. 15, 2016 (KR) .................. 10-2016-0005245

(51) Int. Cl.
| | |
|---|---|
| *B01L 3/00* | (2006.01) |
| *A61M 27/00* | (2006.01) |
| *A61F 5/44* | (2006.01) |
| *B65D 83/10* | (2006.01) |
| *B65D 81/02* | (2006.01) |
| *B65D 25/04* | (2006.01) |
| *G01N 33/493* | (2006.01) |

(52) U.S. Cl.
CPC .................. *B01L 2200/0605* (2013.01); *B01L 2200/0689* (2013.01); *B01L 2300/0832* (2013.01); *B01L 2300/0854* (2013.01); *B01L 2300/0864* (2013.01); *B01L 2400/0644* (2013.01); *B65D 25/04* (2013.01); *G01N 33/493* (2013.01)

(56) References Cited

U.S. PATENT DOCUMENTS

| | | | | |
|---|---|---|---|---|
| 4,084,937 | A * | 4/1978 | Beach | A61B 10/007 |
| | | | | 220/501 |
| 4,981,144 | A * | 1/1991 | Carels, Jr. | A61B 5/14507 |
| | | | | 141/237 |
| 5,087,251 | A * | 2/1992 | Heyman | A61F 5/4408 |
| | | | | 604/327 |
| 2014/0213934 | A1 | 7/2014 | Ellis et al. | |

FOREIGN PATENT DOCUMENTS

| | | |
|---|---|---|
| KR | 10-2010-0101407 | 9/2010 |
| KR | 10-2011-0007813 | 12/2011 |
| KR | 10-2015-0055298 | 5/2015 |

* cited by examiner

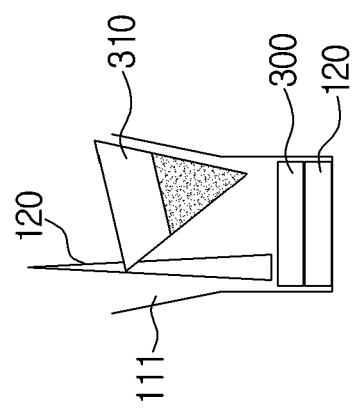
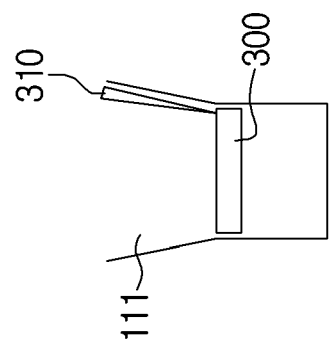

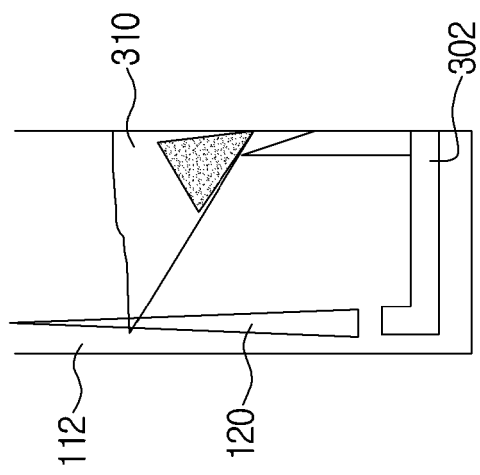
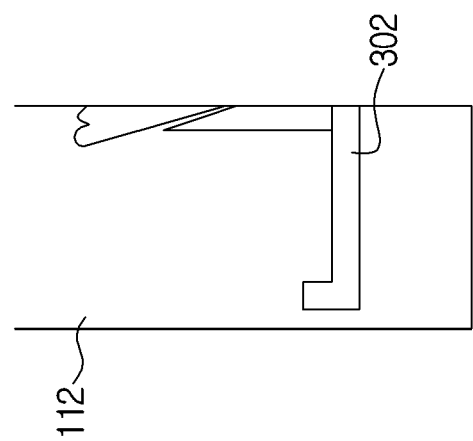
FIG. 5A
FIG. 5B

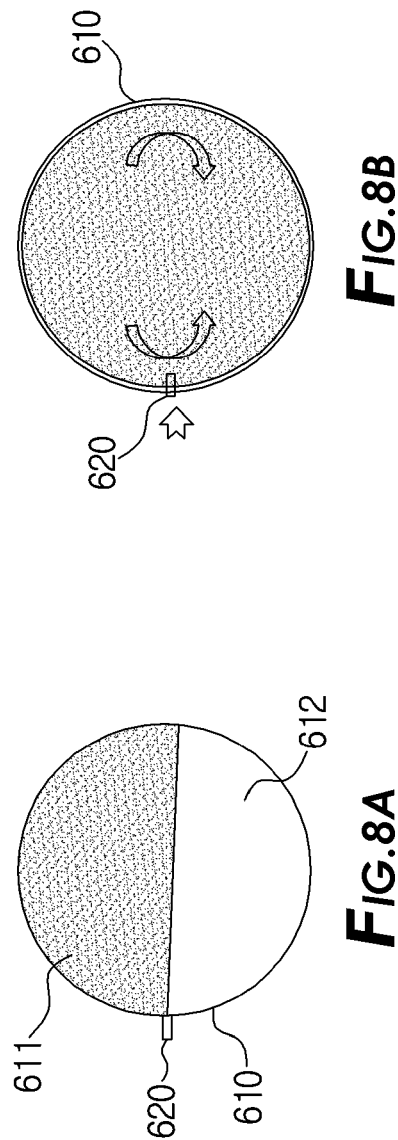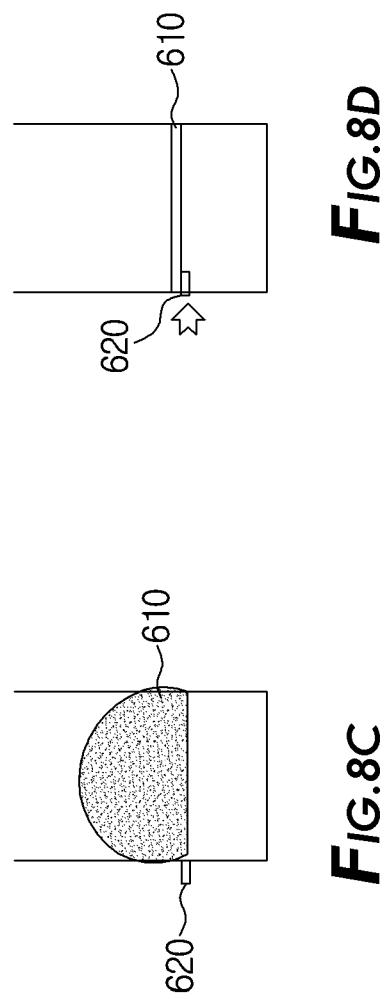

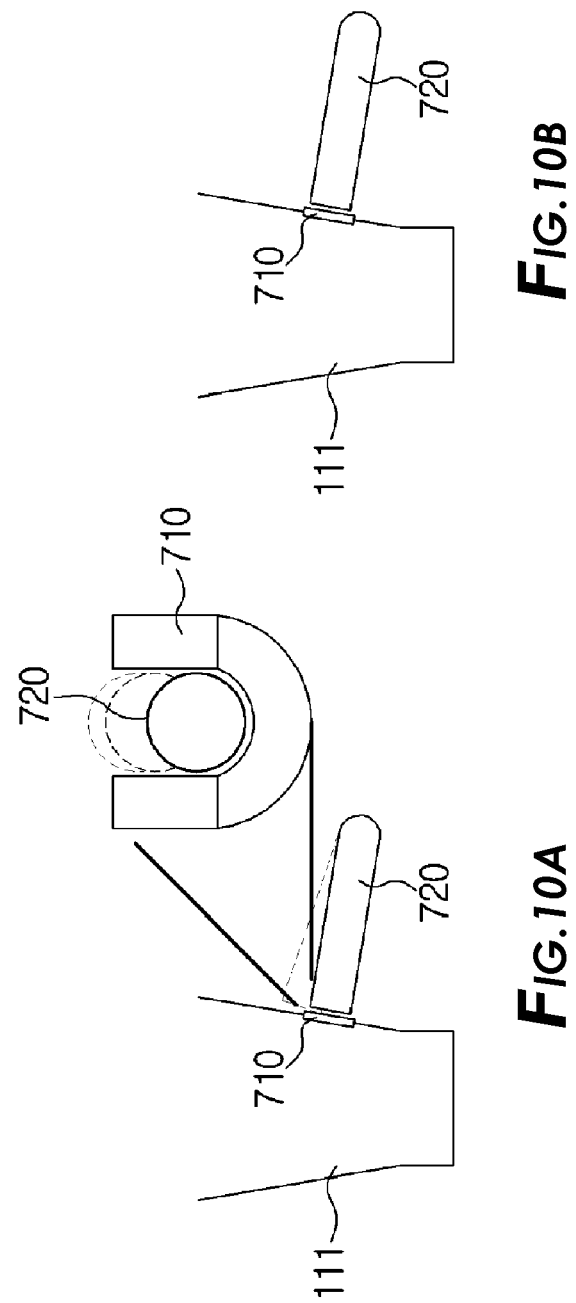

URINE TEST CONTAINER FOR URINE SEPARATION AND INFECTION CONTROL

CROSS-REFERENCE TO RELATED APPLICATION

The present application claims priority to and the benefit of Korean Patent Application No. 10-2015-00155798 filed in the Korean intellectual Property Office on Jun. 11, 2015, the entire contents of which are incorporated herein by reference.

BACKGROUND

(a) Technical Field

The present invention relates to a urine container for the urine test. Since the urine used in the urine test for diagnostic purposes in medical institutes includes a plurality of epithelial cells which decrease test qualities, the first portion of a urine stream is commonly discarded and the rest thereof is then collected in a container. Therefore the present invention particularly relates to a urine container for collecting the whole voided urine but for easily separating the first portion of a urine stream, thereby improving the above described inconvenience.

(b) Description of the Related Art

In general, when patients visit hospitals or clinics, they should have basic tests including X-ray examinations, Electrocardiograms, urine tests etc., to establish plans for diagnosing and treating disease.

Among the above tests, the urine test is, as a clinical pathology examination, essential enough to occupy 30% of the total quantities of tests performed in the most hospitals or clinics, thereby easily collecting urine specimens without suffering patients. Additionally, it is used as an important clinical index when establishing plans for diagnosing and treating diseases which are related to kidney and urinary track diseases, cardiac or endocrine glands diseases, or diseases related to functions of other various organs. Thus, it is recognized as a kind of routine tests essentially to be performed.

Herein, the urine test is a kind of diagnostic methods to diagnose physical conditions and lesions by analyzing urine substances. Since metabolites are voided into kidneys which generate urine and also into the urine, from the whole body, it is widely used to diagnose not only urinary diseases but also systemic diseases.

Generally there are various kinds of clinical urine tests. Among them, the most basic urine test is performed through Dipstick test which is capable of simultaneously checking up on total 10 of clinical indexes (glucoses, proteins, occult bloods, acid levels, etc.), and determines whether clinically normal or not, with the naked eye or through automatic determination by an analytical instrument.

Infection urine is verified by counting either the number of leukocytes per field through microscope observation or the number of erythrocytes per field when occult bloods are observed in a stick.

At this time, since the distribution of epithelial cells, as a sort of urine substances, decreases the quality of microscope observation, it can be avoided by discarding the first portion of a urine stream (approximately a third of the voided urine; in general, approximately 2 cc in the case of an adult) and then using the rest thereof (Min. 4 cc). Thus, subjects are instructed to discard the first portion of a urine stream and then to fill a paper cup with urine as much as a marking thereon.

However, when subjects have a urinary incontinence symptom or they are young (a child) or old and weak, it is inconvenient for them to hold their urine to collect the rest stream of voided urine after discarding the first portion thereof. Further, when subjects are infants, paralyzed patients or unconscious patients, it is impossible for them to be tested. Alternatively, it can be happened that subject's hand is smeared with urine when he/she tries to position a paper cup at the genital organ (the external genitals), or he/she drips it down.

Further, subjects are instructed that the amount of the first portion of a urine stream is approximately a third of the whole amount of voided urine. However, the determination thereon is frequently based on tester's subjective determination. Hardly can the rest of the urine stream be, thus, collected enough. Alternatively, when discarding a small amount of the first portion of a urine stream, epithelial cells are removed not enough from the voided urine. Therefore, there is a limit to the reliability of results of the test.

Further, when a test operator manually transfers a urine specimen from a urine collection paper cup to a urine cup or a urine tube, there can be any incidences of contamination by dripping it or smearing the surrounding therewith, or of mixing with other specimens.

Therefore, solutions have been required to overcome the above problems.

SUMMARY OF THE INVENTION

Various aspects of the present invention are directed to providing a urine container for collecting the whole voided urine but for easily separating the first portion of a urine stream, thereby improving inconvenience to commonly discard the first portion of a urine stream and then to collect the rest thereof in a container because the urine used in the urine test for diagnostic purposes in medical institutes includes a plurality of epithelial cells which decrease test qualities.

In one aspect of the present invention, provided is a container for removing epithelial cells sufficiently from the whole voided urine to be tested, without artificially discarding the first portion of a urine stream, thereby reducing subject's suffering for stopping the flow of urine due to a urinary incontinence symptom in the middle of urination, and preventing subject's hand from being smeared with urine when he/she tries to position a paper cup at the genital organ (the external genitals), or preventing him/her from dripping it down.

In another aspect of the present invention, provided is a container for discarding an accurate amount of the first portion of a urine stream without tester's subjective determination, thereby increasing the quality and reliability of microscopic examinations and securing an sufficient amount of urine from which epithelial cells are removed.

In yet another aspect of the present invention, provided is a container for preventing any incidences of contamination by dripping a urine specimen or mixing with other specimens when a test operator manually transfers it from a urine collection paper cup to a urine cup or a urine tube.

Additional aspect of the present invention provides a container for removing concerns on timely test that urine specimens are ordinary analyzed within 2 hours after specimen collection, or are refrigerated.

To achieve in the present invention are not limited to the technical problems mentioned above, in another aspect not covered will be clearly understood to those of ordinary skilled in the art from the following description.

An exemplary embodiment of the present invention provides a urine container for collecting urine from a subject, which may include: a urine container for collecting urine; and a blocking layer which is positioned inside the urine container and partitions the inside thereof, so as to separate a predetermined amount of a first stream initially collected from the urine and a second stream of the urine, wherein only the second stream is used in the urine test of the subject, and the second stream may be separated by using the first stream and the blocking layer.

Further, the blocking layer may include: a rotary shaft which is connected to the urine container and then fixed thereto; and a blocking layer which is formed in parallel to the rotary shaft and rotates around the rotary shaft, wherein the first stream is collected in the lower portion of the blocking layer through rotation of the blocking layer, and if the first stream collected to the region where the blocking layer is placed, rotation of the blocking layer is shut off by the first stream, and the second stream may be collected in the upper portion of the blocking layer separately from the first stream.

Further, the blocking layer may be configured to up and downwardly couple a first blocking layer where the plurality of holes are formed in a first placement type and a second blocking layer where a plurality of holes in a second placement type that is different from the first placement type, wherein at least one of the first and second blocking layers is rotatable or movable, and the second stream may be collected through the rotation and movement, separately from the first stream.

Further, the container may include a first region of which a middle region is narrower than other regions, wherein the blocking layer has a ball shape with a width wider than that of the first region, is placed in the second region positioned in the lower portion of the first region among the whole regions of the container, and rises when the urine is collected in the second region, and the risen blocking layer is coupled with the first region, thereby collecting the second stream, separately from the first steam.

Further, the container may be equipped with an openable coupling hole, on the lower side surface where the second stream is contained, and may further include a urine cup which has a width corresponding to that of the coupling hole and is inserted into the opened coupling hole and then fixed thereto when the coupling hole is opened. The second stream may be moved to the urine cup without any contamination.

Further, the blocking layer may be detached from the container.

Further, the container may further include an absorbent for absorbing the first stream, in the lower portion of the container.

Further, the container may further include an additional container into which the container is inserted, wherein at least one hole is formed on the lower portion of the container, the first stream is discharged through the at least one hole, the discharged first stream is contained in the additional container, and the additional container coupled with the container may be detachable therefrom.

Meanwhile, another exemplary embodiment of the present invention provides a urine container for collecting urine from a subject, which may include: a container for collecting the urine; and a blocking layer which is positioned inside the container and partitions the inside thereof, thereby separating a predetermined amount of a first stream from initially collected urine and a second stream of the urine, wherein only the second stream is used in the urine test of a subject, and the second stream may be separated by external pressures or forces by at least one of a user and the first stream.

Further, the container may further include a plastic bag, wherein if the position of the blocking layer is moved down by external pressures or forces of at least one of a user and the first stream, the plastic bag is opened and the second stream may be collected in the opened plastic bag, separately from the first stream.

Further, the blocking layer may include: a fixed first region; and a second region which rotates around a rotary shaft formed on the end portion of the first region; and it may further include a driving device which is equipped to the at least part of the container to induce rotation, and if the blocking layer is modified into a lid shape clogged by rotation of the second region through the operation of the driving device, the second stream may be collected separately from the first stream by using the modified shape of the blocking layer.

Further, the container may be equipped with an openable coupling hole, on the lower side surface where the second stream is contained, and it may further include a urine cup which has a width corresponding to that of the coupling hole and is inserted into the opened coupling hole and then fixed thereto when the coupling hole is opened, wherein the second stream is moved to the urine cup without any contamination.

Further, the blocking layer may be detachable from the container.

Further, the container may further include an absorbent for absorbing the first stream, in the lower portion of the container.

Further, the container may further include an additional container into which the container is inserted, wherein at least one hole is formed on the lower portion of the container, the first stream is discharged through the at least one hole, the discharged first stream is contained in the additional container, and the additional container coupled with the container may be detachable therefrom.

According to an exemplary embodiment of the present invention, a urine container is capable of collecting the whole voided urine but of easily separating the first portion of a urine stream, thereby improving inconvenience to commonly discard the first portion of a urine stream and then to collect the rest thereof in a container because the urine used in the urine test for diagnostic purposes in medical institutes includes a plurality of epithelial cells which decrease test qualities.

In particular, according to an advanced urine container of the present invention, it is possible to perform urine tests for subjects who have a urinary incontinence symptom and thus for whom it is hard to hold their urine compared to ordinary peoples, for subjects who are women, young or old and weak peoples or the obese, and for subjects for whom it is basically impossible to perform the urine test, such as infants, paralyzed patients or unconscious patients.

In addition, according to the present invention, it is possible to separate the first stream of the urine from the whole voided urine in the accurately predetermined amount of 1.5 cc, 2 cc, 2.5 cc, etc., not based on tester's subjective determination.

Further, according to the present invention, it is not needed for subjects to position a paper cup for the urine test, at the genital organ while they are urinating, thereby preventing the circumference of the paper cup from any contamination.

Ultimately, according to the present invention, it is possible to separate unnecessary substances including glucose, ketone body, bilirubin, occult blood, leukocyte, etc., which are present in the first portion of the urine stream, and affect the urine analysis in the urine test for health medical examination or early detection of diseases. It is also possible to easily control subject's infection.

Further, according to the present invention, it is possible to accurately separate the first portion of a urine stream, thereby removing apprehensions regarding re-tests, and timing the urine test.

Further, according to the present invention, a container can be easily manufactured, and widely used in all institutions which perform the urine test.

Further, according to the present invention, it is possible to provide an additional apparatus for containing the collected urine to be used in the urine test, without any additional contaminations when transferring the urine to a urine cup or a urine tube.

Effects of the present invention are not limited to the effects mentioned above, in another aspect not covered will be clearly understood to those of ordinary skilled in the art from the following description.

Meanwhile, according to the present invention, a urine blocking layer 302 can be manufactured in a state of coupling with the urine container 110, while it may have a structure that is detachable from the urine container 110.

That is, the blocking layer 320 manufactured in a detachable type can be coupled with the urine container 110 only if necessary, and then used. After being used, it can be detached therefrom.

For instance, if the urine container 110 is a paper cup, it can be used normally as a usual paper cup. On the other hand, it can be used for urine test purposes by coupling the blocking layer 320 with the urine cup 110, only if the urine test is necessary.

Further, according to the present invention, it is possible to provide a structure capable of absorbing the first portion of a urine stream through an absorbent.

Further, according to the present invention, it is possible to provide a structure to couple a plurality of holes formed on the lower portion of the urine container, the urine container and the additional container, thereby automatically discharging the separated first portion of a urine stream into the additional container.

BRIEF DESCRIPTION OF THE DRAWINGS

FIG. 4 depicts yet another particular exemplary embodiment of a urine container according to the present invention.

FIG. 5 depicts yet another particular exemplary embodiment of a urine container according to the present invention.

FIG. 8 depicts yet another particular exemplary embodiment of a urine container according to the present invention.

FIG. 10 depicts a particular exemplary embodiment of the present invention, wherein a urine cup or a urine tube is equipped on the lower side surface of a urine container containing the second stream for the urine test, so as to contain the urine without any contamination.

Figure 12A:
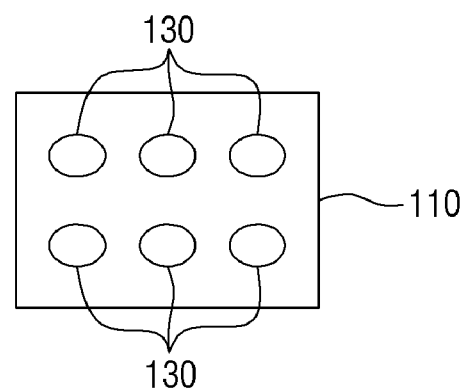
Figure 12B:
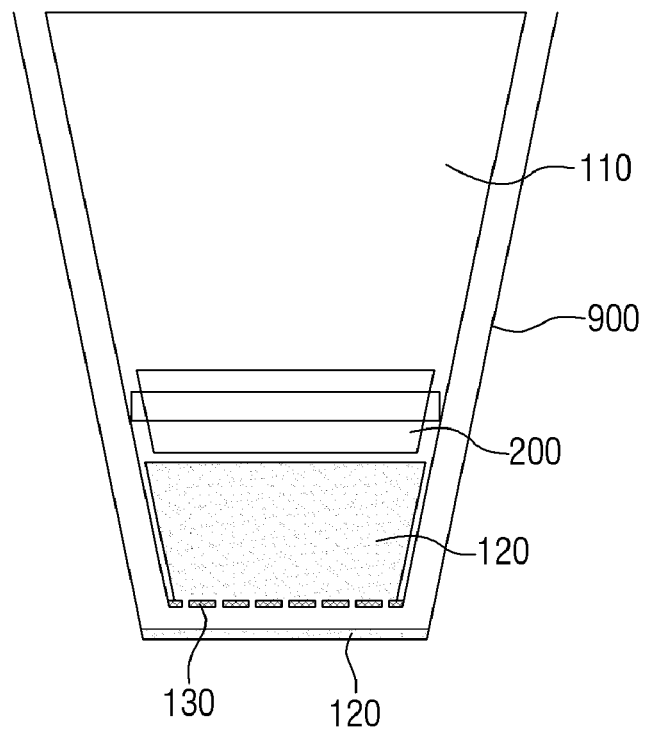

Respective (a) and (b) of FIG. 12 depict a particular exemplary embodiment of a structure according to the present invention, wherein a plurality of holes formed on the lower portion of a urine container 110, the urine container 110 and an additional container 900 are coupled together so that the separated first portion of a urine stream 120 is automatically discharged into the additional container.

DETAILED DESCRIPTION OF THE EMBODIMENTS

In general, when patients visit hospitals or clinics, they should have basic tests including X-ray examinations, Electrocardiograms, urine tests etc., to establish plans for diagnosing and treating disease.

Among the above tests, the urine test is, as a clinical pathology examination, essential enough to occupy 30% of the total quantities of tests performed in the most hospitals or clinics, thereby easily collecting urine specimens without suffering patients. Additionally, it is used as an important clinical index when establishing plans for diagnosing and treating diseases which are related to kidney and urinary track diseases, cardiac or endocrine glands diseases, or diseases related to functions of other various organs. Thus, it is recognized as a kind of routine tests essentially to be performed.

Herein, the urine test is a kind of diagnostic methods to diagnose physical conditions and lesions by analyzing urine substances. Since metabolites are voided into kidneys which generate urine and also into the urine, from the whole body, it is widely used to diagnose not only urinary diseases but also systemic diseases.

Generally, there are various kinds of clinical urine tests. Among them, the most basic urine test is performed through Dipstick test which is capable of simultaneously checking up on total 10 of clinical indexes (glucoses, proteins, occult bloods, acid levels, etc.), and determines whether clinically normal or not, with the naked eye or through automatic determination by an analytical instrument.

Figure 1A:
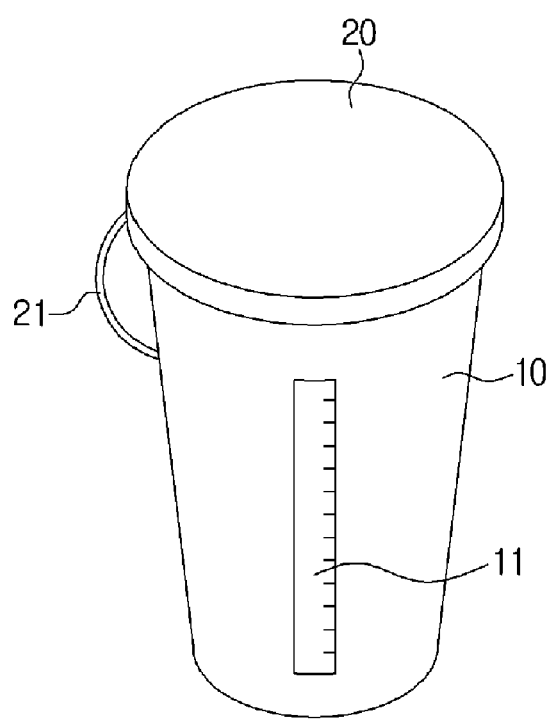
FIGS. 1A and 1B depict one exemplary embodiment of a conventional urine container related to the present invention.
Figure 1B:
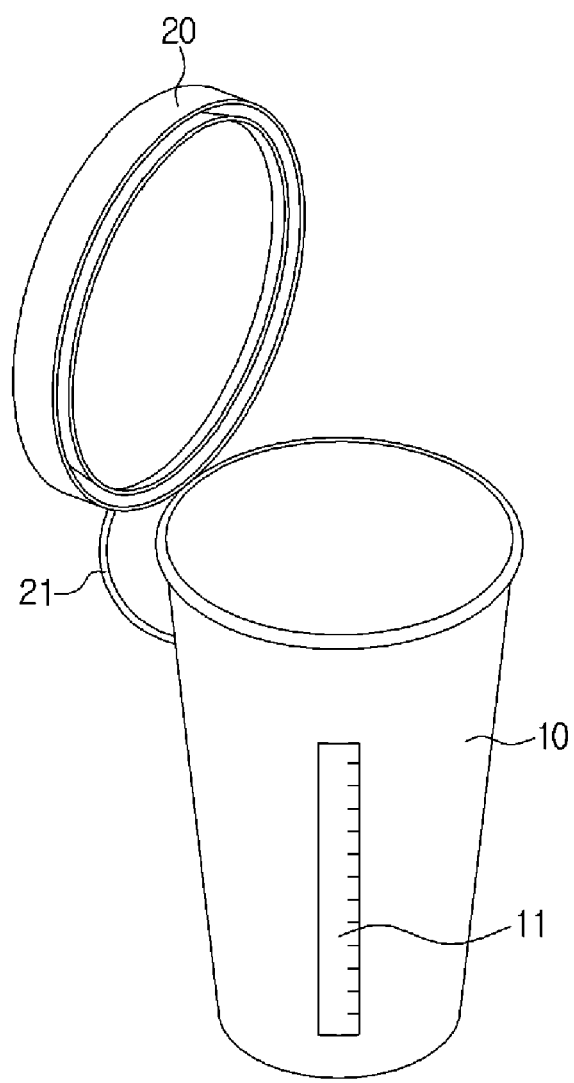
Figure 2A:
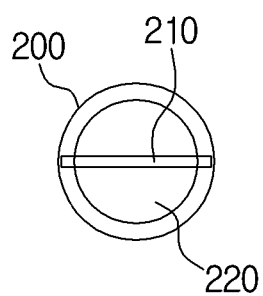
FIG. 2 depicts a particular exemplary embodiment of a urine container according to the present invention.
Figure 2B:
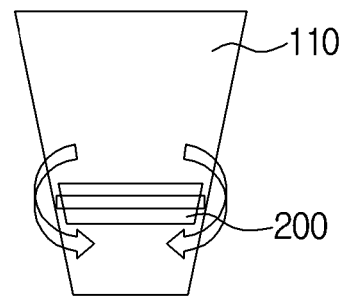
Figure 2C:
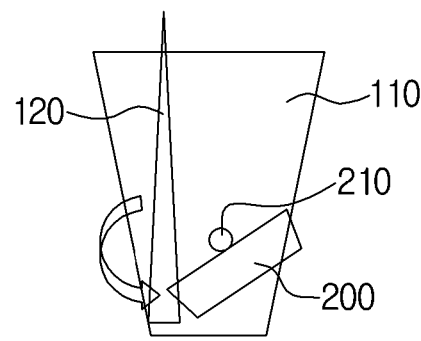
Figure 2D:
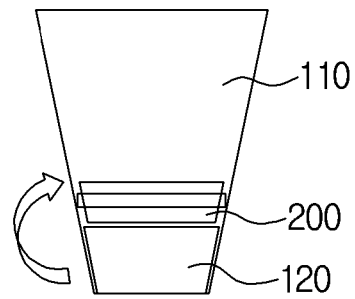

FIGS. 1A and 1B depict a particular exemplary embodiment of an apparatus to be applied to these urine tests.

Referring to FIGS. 1A and 1B, a main body of a container 10 having a cylindrical shape of which top portion is opened is made of paper and equipped with a sight glass 11 formed in a longitudinal direction on the side wall, thereby seeing through the inside thereof. Particularly, the sight glass 11 has markings to confirm the amount of the urine.

Further, a vinyl coating layer for waterproof is preferably formed inside the main body of the container 10.

Meanwhile, a lid 20 is detachably formed on the top portion of the main body of the container 10, wherein the lid 20 is coupled thereto in one body by a soft coupling part 21, thereby preventing from being lost.

The urine container depicted in FIGS. 1A and 1B is generally used for health medical examination in hospitals or clinics. A subject opens the lid 20 coupled to the top portion of the main body of the container, and then fills the container with a predetermined amount of urine.

At this time, a subject can confirm the amount of urine directly with the naked eye through the sight glass 11 with markings, which is formed on the side wall of the main body of the container 10, thereby filling the container with a desired amount of urine.

Additionally, when the container is filled with a predetermined amount of urine, the container is closed with the lid 20, thereby preventing the inflow of foreign substances simultaneously with inconveniences by the outflow or stink of the urine caused by shaking while being transferred.

As using the urine container of FIGS. 1A and 1B, it is possible to easily control the amount of urine as much as to be desired and also to store it more hygienically.

However, conventional containers which are currently applied to urine tests, such as the urine container of FIGS. 1A and 1B, have drawbacks.

Infection urine is verified by counting either the number of leukocytes per field through microscope observation or the number of erythrocytes per field when occult bloods are observed in a stick. At this time, since the distribution of epithelial cells, as a sort of urine substances, decreases the quality of microscope observation, it can be avoided by discarding the first portion of a urine stream (approximately a third of the voided urine; in general, approximately 2 cc in the case of an adult) and then using the rest thereof (Min. 4 cc). Thus, subjects are instructed to discard the first portion of a urine stream and then to fill a paper cup with urine as much as a marking thereon.

However, when subjects have a urinary incontinence symptom or they are young (a child) or old and weak, it is inconvenient for them to hold their urine to collect the rest stream of voided urine after discarding the first portion thereof. Further, when subjects are infants, paralyzed patients or unconscious patients, it is impossible for them to be tested. Alternatively, it can be happened that subject's hand is smeared with urine when he/she tries to position a paper cup at the genital organ (the external genitals), or he/she drips it down.

Further, subjects are instructed that the amount of the first portion of the urine stream is approximately a third of the whole amount of the voided urine. However, the determination thereon is frequently based on tester's subjective determination. Hardly can the rest of urine stream be, thus, collected enough. Alternatively, when discarding a small amount of the first portion of the urine stream, epithelial cells are removed not enough from the voided urine.

Further, when a test operator manually transfers a urine specimen from a urine collection paper cup to a urine cup or a urine tub, there can be any incidences of contamination by dripping it or smearing the surrounding therewith, or of mixing with other specimens.

Accordingly, in order to solve the above described drawbacks, the present invention provides a urine container for collecting the whole voided urine but for easily separating the first portion of a urine stream, thereby improving inconvenience to commonly discard the first portion of a urine stream and then to collect the rest thereof in a container because the urine used in the urine test for diagnostic purposes in medical institutes includes a plurality of epithelial cells which decrease test qualities.

Further, in one aspect of the present invention, provided is a container for removing epithelial cells sufficiently from the whole voided urine to be tested, without artificially discarding the first portion of a urine stream, thereby reducing subject's suffering for stopping the flow of urine due to a urinary incontinence symptom in the middle of urination, and preventing subject's hand from being smeared with urine when he/she tries to position a paper cup at the genital organ (the external genitals), or preventing him/her from dripping it down.

In another aspect of the present invention, provided is a container for discarding an accurate amount of the first portion of the urine stream without tester's subjective determination, thereby increasing the quality and reliability of microscopic examinations and securing an sufficient amount of urine from which epithelial cells are removed.

In yet another aspect of the present invention, provided is a container for preventing any incidences of contamination by dripping a urine specimen or mixing with other specimens when a test operator manually transfers it from a urine collection paper cup to a urine cup or a urine tube.

Additional aspect of the present invention provides a container for removing concerns on timely test that urine specimens are ordinary analyzed within 2 hours after specimen collection, or are refrigerated.

Hereinafter, particular configurations of the present invention will be described with reference to particular exemplary embodiments.

The First Exemplary Embodiment of the Present Invention

The first exemplary embodiment of the present invention is directed to a container for easily collecting the urine necessary for the urine test in a state that a blocking layer rotates around a rotary shaft and then blocks a predetermined amount of an initial stream.

Referring to FIG. 1 and FIG. 2, the above first exemplary embodiment is described specifically.

Referring to (a) of FIG. 2, a blocking layer 200 provided in the present invention is depicted.

The blocking layer 200 according to the first exemplary embodiment is composed of a rotary shaft 100 and a blocking layer 220.

That is, the blocking layer 220 can be moved by vertically rotating around the rotary shaft 210.

(b) of FIG. 2 depicts that the aforementioned blocking 200 is coupled to a urine container 110.

Further, (c) of FIG. 2 depicts that when a user fills a urine container 110 with urine 120, the urine is contained in the lower portion of the blocking layer 200 by vertical rotation of the blocking layer 220 around the rotary shaft 210.

Further, (d) of FIG. 2 depicts that when the lower portion of the blocking layer 200 is fully filled with the urine 120, rotation is stopped, and the upper portion of the blocking layer is then filled with urine to be used for the urine test.

Figure 3:
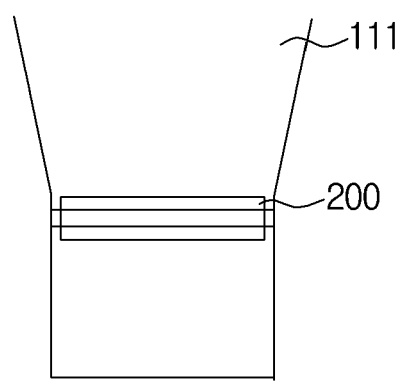
FIG. 3 depicts another particular exemplary embodiment of a urine container according to the present invention.

Meanwhile, FIG. 3 depicts an exemplary embodiment of a urine container 111 which is applied with the same configuration as the container described in FIG. 2 but has a different shape therefrom.

That is, compared to FIG. 2, the lower portion of the blocking layer 200 is configured to be a perpendicular shape in FIG. 3.

Through the aforementioned first exemplary embodiment, provided is a urine container for collecting the whole voided urine but for easily separating the first portion of a urine stream, thereby improving inconvenience to commonly discard the first portion of the urine stream and then to collect the rest thereof in a container because the urine used in the urine test for diagnostic purposes in medical institutes includes a plurality of epithelial cells which decrease test qualities.

That is, according to an advanced urine container of the present invention, it is possible to perform urine tests for subjects who have a urinary incontinence symptom and thus for whom it is hard to hold their urine compared to ordinary peoples, for subjects who are women, young or old and weak peoples or the obese, and for subjects whom it is basically impossible to perform the urine test for, such as infants, paralyzed patients or unconscious patients.

The Second Exemplary Embodiment of the Present Invention

The second exemplary embodiment of the present invention is directed to a container for easily collecting the urine necessary for the urine test, wherein a blocking layer is squashed by pressure due to a predetermined amount of urine and then a plastic bag is automatically opened.

Referring to FIGS. 4 and 5, the above second exemplary embodiment is described specifically.

Referring to (a) of FIG. 4, a container is equipped with a folded plastic bag 310 in the upper portion of a blocking layer 300 which is formed in the middle region of the urine container 111 according to the present invention.

At this time, when a user fills the urine container 111 with urine 120, the blocking layer 300 is squashed downwardly by increased weights of the urine 120, and then the blocking layer 300 is moved to the lower portion. Thus, the folded plastic bag 310 is opened as like in (b) of FIG. 4 and the urine 120 is contained therein.

Therefore, a part amount of an initial stream is positioned in the lower portion of the blocking layer 300, and then only following urine is contained in the plastic bag 310, thereby overcoming conventional drawbacks.

FIG. 5 depicts a container having the same structure as that of FIG. 4, wherein a blocking layer 302 capable of easily folding and opening the plastic bag 310 is adopted.

As shown in (a) of FIG. 5, the end portion of the blocking layer 302 corresponds to the end portion of the plastic bag 310, so as to form a shape for more safe folding.

Further, when a user fills the urine container 112 with the urine 120, blocking layer 302 is squashed downwardly by increased weights of the urine 120, and then the blocking layer 302 is moved to the lower portion. Thus, the folded plastic bag 310 is opened as like in (b) of FIG. 5 and the urine 120 is contained therein. At this time, compared to (b) of FIG. 4, since the end portion thereof is hung up on the blocking layer 302, it is easily opened as an advantage.

Through the aforementioned second exemplary embodiment, it is not needed for subjects to position a paper cup for the urine test, at the genital organ while they are urinating, thereby preventing the circumference of the paper cup from any contamination.

That is, it is possible to separate unnecessary substances including glucose, ketone body, bilirubin, occult blood, leukocyte, etc., which are present in the first portion of the urine stream, and affect the urine analysis in the urine test for health medical examination or early detection of diseases. It is also possible to easily control subject's infection.

The Third Exemplary Embodiment of the Present Invention

The third exemplary embodiment of the present invention is directed to a container for easily blocking a predetermined amount of urine by turning a blocking layer by a user, wherein the blocking layer having a plurality of holes is configured to be a double-layer structure.

Figure 6B:
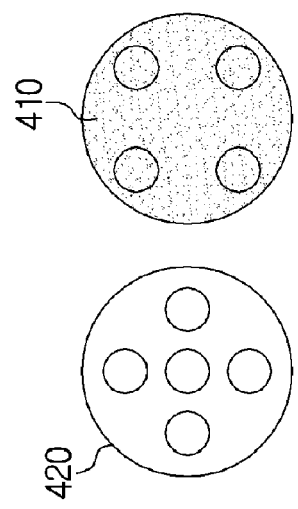
FIG. 6 depicts yet another particular exemplary embodiment of a urine container according to the present invention.
Figure 6C:
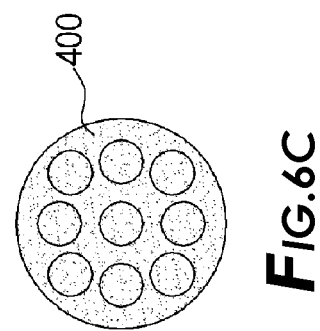
Figure 6A:
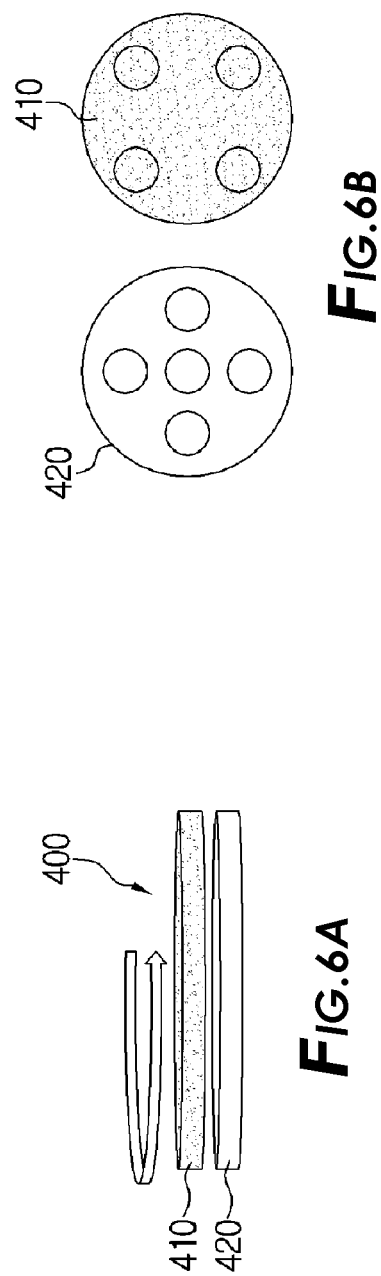

Referring to FIG. 6, the above third exemplary embodiment is described specifically.

All the same structures described in the first and second exemplary embodiments are applied to the third exemplary embodiment.

When configuring the blocking layer in a double-layer structure, a plurality of holes are displaced on each of the blocking layers, differently from each other, thereby supporting a user in separation/collection of urine.

Referring to (a) of FIG. 6, a blocking layer 400 according to the present invention is depicted.

The blocking layer 400 according to the third exemplary embodiment is composed of a first blocking layer 410 and a second blocking layer 420.

The blocking layer 400 having a double-layer structure is merely described in this description. However, it is obvious that all blocking layers 400 having a multiple-layer structure, such as triple-layer, quadruple-layer, etc., can be applied to the present invention.

At this time, the first blocking layer 410 and the second blocking layer 420 include a plurality of holes, wherein the first blocking layer 410 and the second blocking layer 420 are positioned in different regions.

That is, as depicted in (b) of FIG. 6, respective holes of the first blocking layer 410 and the second blocking layer 420 are placed into different placement types.

Further, a user turns one of the first blocking layer 410 and the second blocking layer 420 to prevent the holes of the first blocking layer 410 and the second blocking layer 420 from being overlapped.

A schematic view thereof is depicted in (c) of FIG. 6.

Therefore, as a user turns one of the first blocking layer 410 and the second blocking layer 420, when a predetermined amount of urine is contained, the blocking layer 400 blocks following urine, thereby separately collecting the urine necessary for the urine test.

The Fourth Exemplary Embodiment of the Present Invention

The fourth exemplary embodiment of the present invention is directed to a container for easily collecting the urine necessary for the urine test, wherein the container has a certain region formed to be narrow and is equipped with a ball corresponding to the size of the narrow region. When a predetermined amount of urine is contained, a middle region is clogged with the ball, thereby easily collecting the urine necessary for the urine test.

Figure 7B:
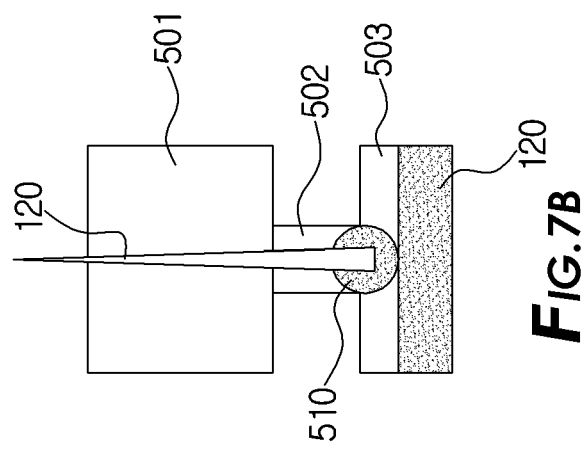
FIG. 7 depicts yet another particular exemplary embodiment of a urine container according to the present invention.
Figure 7A:
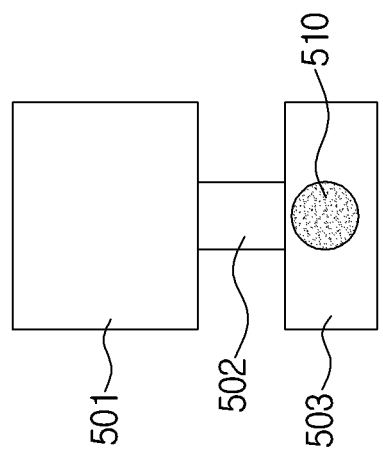

Referring to (a) of FIG. 7, the above fourth exemplary embodiment of the present invention is described specifically.

Referring to (a) of FIG. 7, a urine container according to the present invention is depicted, wherein the urine container is composed of a first region 501, a second region 502 and a third region 503.

At this time, the second region 502 has a wide area compared to those of the first region 501 and the third region 503.

Further, the third region 503 includes a ball shaped blocking layer 510 of which at least part has at least partially bigger size than that of the second region 502.

When a user fills the urine container with urine, as filling the third region 503 with the urine 120, the ball shaped blocking layer 510 rises over the surface of the urine. Consequently, it is inserted into the lower portion of the second region 502 and then fixed.

When the ball shaped blocking layer 510 is inserted into the second region 502, the urine 120 does not flow down to the third region 503 but is collected in the first region 501 and the second region 502.

Therefore, the user can easily separate a predetermined amount of urine and then collect the urine to be used for the urine test.

The Fifth Exemplary Embodiment of the Present Invention

The fifth exemplary embodiment of the present invention is directed to a container for easily collecting the urine necessary for the urine test, by blocking a predetermined amount of an initial stream by rotating a blocking layer formed into a lid shape, around a rotary shaft.

Figure 9B:
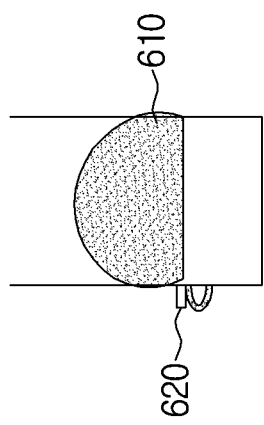
FIG. 9 depicts yet another particular exemplary embodiment of a urine container according to the present invention.
Figure 9A:
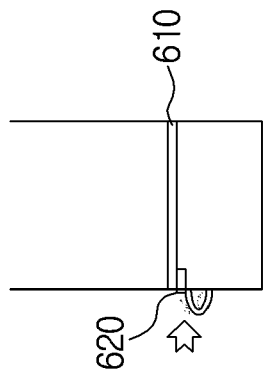

Referring to FIG. 8 and FIG. 9, the above fifth exemplary embodiment is described specifically.

All the same structures described in the first and second exemplary embodiments are applied to the fifth exemplary embodiment.

A blocking layer 610 is manufactured into a lid shape, a first region 611 thereof is fixed, and a second region 612 thereof vertically rotates around a central axis.

Further, to press a rotation button becomes a trigger signal, thereby operating rotation of the second region 612.

When a user presses a button 620 of which the shape is depicted in (a) of FIG. 6, the second region 612 is closed by vertically rotating. Thus, the blocking layer 610 becomes a shape of the covered lid.

(c) of FIG. 8 depicts that the blocking layer 610 of (a) of FIG. 8 is included in a urine container. (d) of FIG. 8 depicts that the blocking layer 610 of (b) of FIG. 8 is included in a urine container.

Meanwhile, according to another exemplary embodiment, provided is a grip 630 so that a user easily separates urine.

FIG. 9 depicts a urine container including the grip 630 according to the present invention. (a) and (b) of FIG. 9 correspond (c) and (d) of FIG. 8 respectively, and are additionally equipped with each of the grip 630.

The user uses the grip 630 for lifting the urine container up easily or for discarding a portion where an initial stream is collected.

The Sixth Exemplary Embodiment of the Present Invention

Meanwhile, according to yet another exemplary embodiment of the present invention, a urine cup or a urine tube is equipped on the lower side surface of a container containing a second stream, thereby containing the urine for the urine test without any contamination.

According to the aforementioned first and second exemplary embodiments, a user easily separates a predetermined amount of urine and then collects the urine for the urine test.

At this time, the present invention further provides an apparatus for containing the collected urine for the urine test, without any additional contaminations when transferring the urine to a urine cup or a urine tube. According to the present invention, FIG. 10 depicts a particular exemplary embodiment, wherein a urine cup or a urine tube is equipped on the lower side surface of the container.

Referring to FIG. 10, the urine container 111 according to the first exemplary embodiment is depicted. However, the urine container 111 is only one embodiment of the present invention, and it is obvious that urine containers of other exemplary embodiments are applicable thereto.

The urine container is equipped with a coupling hole 710 on the lower side surface of the urine container 111, to be coupled with a urine cup or a urine tube 720 as depicted in (a) of FIG. 10.

That is, the width of the coupling hole 710 is configured to correspond that of a urine cup or a urine tube as depicted in (a) of FIG. 10. The urine cup or the urine tube 720 is inserted into the coupling hole 710 and then fixed thereto, thereby transferring the urine collected for the urine test to the urine cup or the urine tube 720 without additional contamination as depicted in 9b0 of FIG. 10.

Meanwhile, the coupling hole 710 is closed by a stopper before being coupled with the urine tube or the urine tube 720.

Further, the coupling hole 710 according to the present invention is made of plastics or other similar materials.

That is, when the urine cup or the urine tube 720 is inserted into the side of the urine container 111 for containing the second stream, the plastic coupling hole 710 on the side of the container 111 containing the second stream is opened by insertion forces thereof, and then the second stream is automatically transferred to the urine cup or the urine tube 720.

In conclusion, after collecting an enough amount of the urine for the urine test, the stopper is opened so that the coupling hole 710 becomes an open type and then the urine cup or the urine tube 720 is inserted thereinto, thereby safely transferring the urine for the urine test without any contamination.

The Seventh Exemplary Embodiment of the Present Invention

The present invention relates to a urine container for the urine test. Since the urine used in the urine test for diagnostic purposes in medical institutes includes a plurality of epithelial cells which decrease test qualities, the first portion of a urine stream is commonly discarded and the rest thereof is then collected in a container. Therefore, the present invention particularly relates to a urine container for collecting the whole voided urine but for easily separating the first portion of the urine stream, thereby improving the above described inconvenience.

At this time, the urine for the urine test should be collected in a separated condition of the first portion of a urine stream, wherein it could be a problem how to completely separate the first portion of a urine stream from the urine to be tested.

Accordingly, the seventh exemplary embodiment of the present invention provides an additional method for using an absorbent, and a structure thereof.

Figure 11:
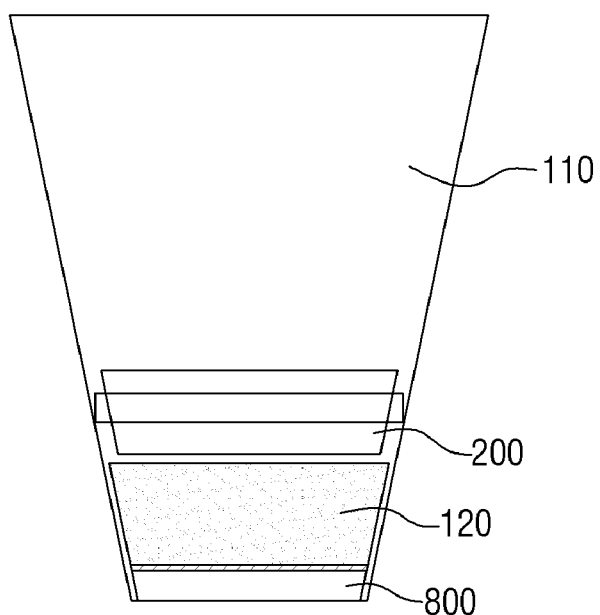
FIG. 11 depicts a particular exemplary embodiment of a structure 800 according to the present invention, wherein the separated first portion of the urine stream is absorbed into an absorbent.

According to the present invention, FIG. 11 depicts a particular exemplary embodiment of a structure for absorbing the first portion of a urine stream which is separated through the absorbent.

FIG. 11 describes a method for using an absorbent through the structure of the first exemplary embodiment of the present invention.

However, the present invention is not limited to first exemplary embodiment, but is applicable to all the second to sixth exemplary embodiments.

Referring to FIG. 11, an absorbent 800 is equipped at the lower portion of a urine container, that is, a section where an initial stream is collected.

It is possible to apply all materials which are capable of absorbing liquid types of urine to the absorbent 800.

Further, as depicted in (c) of FIG. 2, when a user fills the urine container 110 with the urine 120, the lower portion of the blocking layer 200 is filled with the urine by rotating the blocking layer 220 vertically around the rotary shaft, and an initial stream is absorbed through the absorbent 800 which is equipped at the lower portion of the urine container 110.

Therefore, as depicted in (d) of FIG. 2, as the lower portion of the blocking layer 200 is fully filled with the urine 120, it does not rotate any more, and then the upper portion of the blocking layer 200 is filled with the urine for the urine test so that the urine is safely collected because the initial stream has been already absorbed.

The Eighth Exemplary Embodiment of the Present Invention

As described in the seventh exemplary embodiment, the initial urine should be collected in a separated condition of the first portion of a urine stream, wherein it could be a problem how to completely separate the first portion of a urine stream from the urine to be tested.

Accordingly, the eighth exemplary embodiment of the present invention provides a urine container having a plurality of holes on the lower portion thereof, an additional method for using an additional container 900 capable of being inserted into the urine container 100, and a structure thereof.

According to the present invention, FIG. 12 depicts a particular exemplary embodiment of a plurality of holes formed on the lower portion of the urine container 110 and of a structure for automatically discharging, into the additional container, the first portion of a urine stream separated by coupling the urine container 110 and the additional container 900.

As depicted in (a) of FIG. 12, a plurality of holes 130 are formed on the lower portion of the urine container 110.

(c) of FIG. 12 depicts 6 of holes, but the present invention is not limited thereto.

In addition, FIG. 12 describes, as a reference, the first exemplary embodiment of the present invention, but the present invention is not limited thereto.

Referring to the additional container 900 is provided into which the urine container 110 is inserted.

Further, as depicted in (c) of FIG. 2, when a user fills the urine container 110 with the urine 120, the lower portion of the blocking layer 200 is filled with urine by rotating the blocking layer 220 vertically around the rotary shaft, and then the urine flows down through a plurality of holes 130 formed on the lower portion of the urine container 110.

At this time, the first portion of a urine stream is stored in the additional container 900 which is coupled with the urine container 110.

Further, the additional container 900 is detachable form the urine container 110. As like in (d) of FIG. 2, when the lower portion of the blocking layer 200 is fully filled with the urine 120, the blocking layer stops its rotation, and then the upper portion of the blocking layer 200 is filled with the urine for the urine test, wherein an initial stream has been already separated through the additional container 900, thereby safely collecting the urine for the urine test.

In the case of applying the aforementioned configurations of the present invention, the present invention provides a user with a urine container for collecting the whole voided urine but for easily separating the first portion of the urine stream, thereby improving inconvenience to commonly discard the first portion of a urine stream and then to collect the rest thereof in a container because the urine used in the urine test for diagnostic purposes in medical institutes includes a plurality of epithelial cells which thus, decrease test qualities.

In particular, according to an advanced urine container of the present invention, it is possible to perform urine tests for subjects who have a urinary incontinence symptom and thus for whom it is hard to hold their urine compared to ordinary peoples, for subjects who are women, young or old and weak peoples or the obese, and for subjects for whom it is basically impossible to perform the urine test, such as infants, paralyzed patients or unconscious patients.

In addition, according to the present invention, it is possible to separate the first stream of the urine from the whole voided urine in the accurately predetermined amount of 1.5 cc, 2 cc, 2.5 cc, etc., not based on tester's subjective determination.

Further, according to the present invention, it is not needed for subjects to position a paper cup for the urine test, at the genital organ while they are urinating, thereby preventing the circumference of the paper cup from any contamination.

Ultimately, according to the present invention, it is possible to separate unnecessary substances including glucose, ketone body, bilirubin, occult blood, leukocyte, etc., which are present in the first portion of the urine stream, and affect the urine analysis in the urine test for health medical examination or early detection of diseases. It is also possible to easily control subject's infection.

Further, according to the present invention, it is possible to accurately separate the first portion of the urine stream, thereby removing apprehensions regarding re-tests, and timing the urine test.

Further, according to the present invention, a container can be easily manufactured, and widely used in all institutions which perform the urine test.

Further, according to the present invention, it is possible to provide an additional apparatus for containing the collected urine for the urine test, without any additional contaminations when transferring the urine to a urine cup or a urine tube.

Meanwhile, the blocking layer 302 can be manufactured in a state of coupling with the urine container 110, while it may have a structure that is detachable from the urine container 110.

That is, the blocking layer 320 manufactured in a detachable type can be coupled with the urine container 110 only if necessary, and then used. After being used, it can be detached therefrom.

For instance, if the urine container 110 is a paper cup, it can be used normally as a usual paper cup. On the other hand, it can be used for urine test purposes by coupling the blocking layer 320 with the urine cup 110, only if the urine test is necessary.

As described above, the exemplary embodiments of the present invention are provided so that those skilled in the art easily implement and conceive them. Even if the exemplary embodiment of the present invention were referred, it can be understood that those of ordinary skilled in the art may modify or alter the present invention within the scope of the present invention. For instance, those skilled in the art may use each of the above described configurations by combination thereof. Therefore, the present invention is not limited to implementation types described herein, but intends to impose the widest scope conforming to the principals and novel features disclosed herein.

The present invention may be specialized as other characteristic types within the scope of the idea and essential features of the present invention. Accordingly, the above detailed description should be considered as exemplary embodiments, and the interpretation thereof should not be limited. The scope of the present invention should be determined by rationally interpreting claims attached herewith, and all modifications within the scope equivalent to the present invention may be included in the scope of the present invention. The present invention is not limited to implementation types described herein, but intends to impose the widest scope conforming to the principals and novel features disclosed herein. Further, exemplary embodiments are constituted by combination of claims which have no explicit citation relationship in the scope of patent claims, and amendments to claims after application can be included in the scope of claimed inventions of the present invention.

What is claimed is:

1. A urine container for collecting urine from a subject, which comprises:
   a urine container for collecting urine; and
   a partition positioned inside the urine container, wherein the partition is operative to separate an initial amount of the urine from a subsequent amount of the urine; and
   a pocket to form a separated space inside the container that is folded to a side of the container;
   wherein:
      only the subsequent amount is used in a urine test for the subject;
      when the force and/or weight of the urine exceeds a limit, the partition is caused to move; and
      the pocket to form the separated space that is linked to the partition, so that the movement of the partition is operative to spread the pocket out, forming the separated space separating the subsequent amount from the initial amount.

2. The urine container of claim 1, wherein the partition is pivotally mounted within the urine container.

3. The urine container of claim 1, wherein the partition is detachable from the container.

4. The urine container of claim 1, wherein the partition is caused to move from a first position to a second position by bearing more downward force than a weight and/or force capacity limit of the partition, wherein when the partition is in the first position, the pocket is folded to the side of the container, and when the partition is in the second position, the pocket is spread out, forming the separated space.

5. The urine container of claim 4, wherein the first position is an upper position and the second position is a lower position.

6. The urine container of claim 4, wherein in both the first and second positions, the partition is oriented perpendicularly with respect to a bottom of the urine container.

7. The urine container of claim 1, wherein the partition separates the container interior into first and second spaces.

8. The urine container of claim 1, wherein the partition is a blocking layer that catches and holds up to its weight and/or force capacity limit above the partition, but thereafter collapses under the weight and pressure of the urine.

9. The urine container of claim 1, wherein the pocket to form the separated space comprises plastic.

10. The urine container of claim 1, wherein the pocket forming the separated space comprises a vertex.

11. The urine container of claim 10, further comprising a link that links the pocket that forms the separated space to the partition at a point that is offset from the vertex.

12. A urine container for collecting urine from a subject, wherein the container comprises:
    a container for collecting urine;
    a partition positioned inside the container, wherein the partition is operative to separate a first portion of a stream of the urine from a second portion of the stream; and
    a pocket to form a separated space inside the container, the pocket folded to a side of the container;
    a link between the partition and the pocket;
    wherein:
       only the second portion of the stream is used in the urine test of the subject;
       when the force and/or weight of the stream of the urine exceeds a limit, the partition drops, pivots, or collapses, pulling the link downward which in turn spreads the pocket out, creating the separated space;
       after the pocket spreads out to form the separated space, the separated space captures the second portion of the stream.

13. The urine container of claim 12, which further comprises
    a plastic bag, wherein
    if the position of the partition is moved down by the force and/or weight of the stream, the plastic bag is opened and the second portion of the stream is collected in the opened plastic bag, separately from the first portion of the stream.

14. The urine container of claim 12, wherein the partition is pivotally mounted within the urine container.

15. The urine container of claim 12, wherein the partition is caused to move from a first position to a second position by bearing more downward force than the limit, wherein when the partition is in the first position, the pocket to form the separated space is folded to the side of the container, and when the partition is in the second position, the pocket is spread out, forming a separated space.

16. The urine container of claim 15, wherein in both the first and second positions, the partition is oriented perpendicularly with respect to a bottom of the urine container.

17. The urine container of claim 15, wherein the pocket forming the separated space comprises a vertex.

18. The urine container of claim 15, further comprising a link that links the pocket forming the separated space to the partition at a point that is offset from the vertex.

19. The urine container of claim 12, wherein the first position is an upper position and the second position is a lower position.

* * * * *